US010183267B2

(12) United States Patent
Day et al.

(10) Patent No.: US 10,183,267 B2
(45) Date of Patent: Jan. 22, 2019

(54) GAS-TO-LIQUIDS CONVERSION PROCESS USING ELECTRON BEAM IRRADIATION

(71) Applicants: Ashley Day, San Luis Obispo, CA (US); Francis Beland, Topanga, CA (US)

(72) Inventors: M. Ashley Day, San Luis Obispo, CA (US); Francis Beland, Topanga, CA (US)

( * ) Notice: Subject to any disclaimer, the term of this patent is extended or adjusted under 35 U.S.C. 154(b) by 395 days.

(21) Appl. No.: 14/921,817

(22) Filed: Oct. 23, 2015

(65) Prior Publication Data

US 2016/0114305 A1    Apr. 28, 2016

Related U.S. Application Data

(60) Provisional application No. 62/067,623, filed on Oct. 23, 2014.

(51) Int. Cl.
*C07C 2/80* (2006.01)
*C07C 9/14* (2006.01)
(Continued)

(52) U.S. Cl.
CPC ............... *B01J 19/085* (2013.01); *C07C 2/80* (2013.01); *C10G 32/04* (2013.01); *C10L 1/06* (2013.01);
(Continued)

(58) Field of Classification Search
CPC ... B01J 19/085; B01J 2219/0875; C07C 2/80; C10L 1/06; C10L 10/10; C10L 2290/542;
(Continued)

(56) References Cited

U.S. PATENT DOCUMENTS 2,892,946 A * 6/1959 Gale ................. B01J 19/085
204/157.15
4,453,079 A    6/1984 Woodbridge
(Continued)

FOREIGN PATENT DOCUMENTS

DE         4428343 A1 * 2/1996 ............ B01J 19/085
WO    WO 2001/04077      1/2001
(Continued)

OTHER PUBLICATIONS

I.E. Makarov, et al., Radiation-Induced Synthesis of Branched Liquid Alkanes, Radiation Chemistry (2007).
(Continued)

*Primary Examiner* — Nicholas A Smith
*Assistant Examiner* — Colleen M Raphael
(74) *Attorney, Agent, or Firm* — Lewis Brisbois Bisgaard & Smith LLP; Nigamnarayan Acharya

(57) ABSTRACT

A process for converting light alkanes from a natural gas production stream to higher molecular weight hydrocarbons is provided. The method includes transporting the natural gas stream to an electron beam reactor, such as a steel flow-type radiation reactor connected hermetically to an accelerator beam window. The gas stream is exposed to electron beam radiation to generate an upgraded and substantially liquefied hydrocarbon stream. The method then includes transporting the substantially liquefied hydrocarbon stream into a scrubber to remove non-condensed gases. The remaining liquid hydrocarbon stream is then transported as condensate to a distillation tower, where high octane products are separated through fractionation.

15 Claims, 2 Drawing Sheets

(51) Int. Cl.
*C10L 1/06* (2006.01)
*B01J 19/08* (2006.01)
*C10G 32/04* (2006.01)
*C10L 10/10* (2006.01)

(52) U.S. Cl.
CPC ....... *C10L 10/10* (2013.01); *B01J 2219/0875* (2013.01); *C10G 2300/305* (2013.01); *C10L 2270/023* (2013.01); *C10L 2290/06* (2013.01); *C10L 2290/10* (2013.01); *C10L 2290/24* (2013.01); *C10L 2290/36* (2013.01); *C10L 2290/542* (2013.01); *C10L 2290/543* (2013.01); *C10L 2290/548* (2013.01); *C10L 2290/60* (2013.01)

(58) Field of Classification Search
CPC .......... C10L 2270/023; C10L 2290/60; C10L 2290/10; C10L 2290/548; C10L 2290/24; C10L 2290/06; C10L 2290/543; C10L 2290/36; C10G 32/04; C10G 2300/305
See application file for complete search history.

(56) References Cited

U.S. PATENT DOCUMENTS

| | | | |
|---|---|---|---|
| 5,414,176 A | 5/1995 | Amariglio | |
| 5,959,170 A | 9/1999 | Withers, Jr. | |
| 6,229,060 B1 | 5/2001 | Vidal | |
| 6,469,225 B1 | 10/2002 | Basset | |
| 6,500,313 B2 | 11/2002 | Sherwood | |
| 6,727,397 B2 | 4/2004 | Basset | |
| 7,473,814 B2 | 1/2009 | Basset | |
| 7,638,672 B2 | 12/2009 | Coperet | |
| 8,545,602 B2 | 10/2013 | Chance | |
| 8,980,802 B2 | 5/2015 | Togna | |
| 2003/0233019 A1 | 12/2003 | Sherwood | |
| 2005/0288541 A1 | 12/2005 | Sherwood | |
| 2009/0205254 A1* | 8/2009 | Zhu | B01J 19/088 48/127.7 |
| 2010/0108567 A1* | 5/2010 | Medoff | B01J 19/08 204/157.15 |
| 2011/0071331 A1 | 3/2011 | Basset | |
| 2012/0297665 A1* | 11/2012 | Goerz, Jr. | B01J 19/088 422/186.21 |
| 2013/0046124 A1* | 2/2013 | Sirdeshpande | C10L 3/08 585/733 |
| 2014/0165831 A1* | 6/2014 | Taylor | C10G 25/12 95/107 |
| 2016/0152905 A1* | 6/2016 | Kelfkens | C10G 45/00 422/142 |

FOREIGN PATENT DOCUMENTS

| | | |
|---|---|---|
| WO | WO 2003/066552 | 8/2003 |
| WO | WO 2006/060692 | 12/2006 |
| WO | WO 2011/159200 | 12/2011 |

OTHER PUBLICATIONS

A.V. Ponomarev, et al., Election-Beam Radiolysis of Gaseous Propane, Radiation Physics and Chemistry (2002).
Kenneth R. Hall, A New Gas to Liquids (GTL) or Gas to Ethylene (GTE) Technology, Catalysis Today (2005).
Alexandr V, Ponomarev, Gas-To-Liquid Transformation of Alkanes by Electron-Beam Irradiation, Mendeloev (2006).

* cited by examiner

GAS-TO-LIQUIDS CONVERSION PROCESS USING ELECTRON BEAM IRRADIATION

STATEMENT OF RELATED APPLICATIONS

This application claims the benefit of U.S. Ser. No. 62/067,623 filed Oct. 23, 2014. That application is entitled "Gas-To-Liquids Conversion Process Using Electron Beam Irradiation," and is incorporated herein by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

Field of the Invention

The present invention relates to the field of fluid separation in connection with natural gas processing. The present invention further relates to a gas-to-liquids conversion process wherein gaseous alkanes are converted into higher molecular weight hydrocarbons using an electron beam reactor to form a high-octane transportation fuel.

General Discussion of Technology

Much of the world's energy is derived from fossil fuels. Fossil fuels include hydrocarbon fluids produced from subsurface reservoirs. Such fuels are generally referred to as "oil and gas." Fossil fuels also include solid hydrocarbons such as coal, bitumen, lignite, tar and kerogen, which are mined. Solid fossil fuels may be heated for steam generation or electricity generation, or may be pyrolyzed, either in situ or at the surface, to create combustible hydrocarbon fluids.

Hydrocarbon fluids are primarily alkanes, which are molecules consisting only of hydrogen and carbon atoms, with all bonds being single bonds. Alkanes are referred to as "saturated" hydrocarbons as they are saturated with hydrogen. The general formula for saturated hydrocarbons is $C_nH_{2n+2}$ (assuming non-cyclic structures). Saturated hydrocarbons are found as either linear or branched species.

Hydrocarbon fluids are frequently used as petroleum fuel. Most commonly, hydrocarbon fluids are taken through a refining process to form gasoline, diesel, or jet fuel (or naptha). These fuels are generally used as transportation fuels, though lighter hydrocarbon fluids are also frequently used for gas-fired steam or electrical generation. Hydrocarbon gases are also commonly used as heating fuel.

The most common transportation fuel for automobiles in the United States is gasoline. Gasoline is a transparent, petroleum-derived liquid that is used primarily as a fuel in internal combustion engines. It consists mostly of organic compounds obtained by the fractional distillation of petroleum, enhanced with a variety of additives. A 42-gallon barrel of crude oil yields about 19 gallons of gasoline when processed in an oil refinery.

The quality of gasoline as a fuel in internal combustion engines is measured by its octane rating. Gasoline is produced in several grades of octane rating. To acquire the higher octane rating, gasoline is generally derived from "heavier" alkane components such as hexane, heptane, octane, pentane, nonane and decane ($C_6$-$C_{10}$). These components are in liquid form at generally ambient conditions.

In order to refine crude oil into gasoline, the lighter alkane components such as methane and ethane are flashed off. Indeed, in many hydrocarbon production operations the lighter components are never gathered or sold, but are simply burned or "flared" at the surface using a "gas flare."

In essence, a vertical gas flare is a gas combustion device. Gas flares are used in the oil and gas industry at petroleum refineries, natural gas processing plants, offshore oil and gas rigs, and at oil and gas production sites. Partly because of the shale gas production boom in the United States, the price of natural gas is suppressed and remains much lower than that of the liquid crude oil. Accordingly, some production companies do not find it economical to transport natural gas to a gathering facility or to a market. Therefore, much natural gas is simply flared.

As a way to avoid the flaring of natural gas and to transport natural gas to market, some producers have liquefied the product. Various methods have been disclosed for liquefying a natural gas stream to assist in transportation. A common approach is to chill the gas stream into a condensable product. For methane and ethane, this generally reduces the volume by about a 600:1 ratio. However, the energy and capital costs required to achieve liquefaction and then transport natural gas liquids (such as by LNG tanker, LNG truck, or by chilled pipeline) can be high.

Another approach is to convert methane and/or ethane into higher alkane mixtures using a metathesis process. U.S. Pat. No. 5,414,176 discloses a process for converting methane to higher hydrocarbons, in particular to $C_2$ to $C_7$ hydrocarbons. The process successively comprises bringing a gas stream consisting essentially of methane into contact with a catalyst comprising a transition metal dispersed over a support based on refractory oxide, then bringing the catalyst into contact with a stream of hydrogen so as to form a gas mixture of higher hydrocarbons and of hydrogen. The process includes subsequently recovering the gas mixture, and separating the higher hydrocarbons from the hydrogen. It is noted that the process comprises two successive contacting operations of the catalyst.

U.S. Pat. No. 7,473,814 also discloses a process for converting methane into ethane by contacting methane with an alkane metathesis metal catalyst. The metal catalyst is selected from metal hydrides, metal organic compounds and mixtures thereof. In one aspect, the metal is chosen from the lanthanides, the actinides and the metals from Groups 2 to 12 of the Periodic Table of the Elements, so as to produce ethane in a proportion of at least 65% by weight with respect to carbon-containing products formed in the process. The process is said to be a single-step process carried out under conditions involving a non-oxidative catalytic coupling of methane. The process is proposed to provide a degree of selectivity by weight for ethane with respect to carbon-containing products formed.

Additional techniques for upgrading gaseous components, namely ethane, by contacting ethane in a gas stream with a metal catalyst have been disclosed. An illustrative patent documents include U.S. Patent Publ. No. 2011/

0071331 entitled "Process for Converting Ethane Into Liquid Alkane Mixtures," where, ethane is upgraded to alkanes having liquid mixtures of 4 carbon atoms or more. See also International Patent Appl. Nos. WO 2006/060692, WO 2003/066552 and WO 2001/04077 wherein chemical reactions involving a metal catalyst are used to upgrade methane into ethane or higher alkane mixtures.

Another solution is to convert the natural gas into hydrocarbon liquids using chemical processing. Fischer-Tropsch technology converts natural gas into "syngas," which is a mixture of carbon monoxide and hydrogen, followed by reaction to liquid fuels. Available processes for the production of synthesis gas for GTL plants are based on steam reforming, partial oxidation or combinations hereof. Unfortunately, Fischer-Tropsch technology requires a great deal of energy and high temperatures ranging beyond 700° C.

Several years ago a research team at Texas A&M University conceived of a process for converting natural gas into hydrocarbon liquids using a "direct" conversion method. The process is considered "direct" because it does not require the generation of syngas. The process is essentially three reaction steps and two separation steps to produce hydrocarbon liquids. See Kenneth R. Hall, *A New Gas to Liquids (GTL) or Gas to Ethylene (GTE) Technology*, Catalysis Today, Vol. 106, pp. 243-46 (Oct. 15, 2005). However, the end result of this process is primarily ethylene and hydrogen, and not a liquid fuel.

To create a product that has greater commercial value, it is desirable to convert the gaseous alkanes into a liquid transportation fuel without need of a synthesis process or a metal catalyst. Further, a need exists for a process of quickly upgrading a naturally-occurring mixture of lower molecular weight fuels available at many production sites into a high octane transportation fuel without need of large chillers. Further, a need exists for a process for economically upgrading the lower molecular weight hydrocarbons from a gas stream, together into a high-octane liquid gasoline, or into a blend for transportation fuel, at or near a production site.

SUMMARY OF THE INVENTION

A process for converting a gas stream comprising primarily light alkanes into a high-octane liquid stream is first provided. The gas stream is preferably a natural gas production stream acquired in connection with oil and gas production operations.

In one aspect, the process includes introducing the natural gas stream to a reactor. The reactor is an electron beam reactor such as a steel flow-type reactor. The reactor is connected hermetically to an accelerator beam window. Preferably, the natural gas stream has first been sweetened by the removal of any $CO_2$ and any sulfuric components before introduction into the reactor.

In order to introduce the natural gas stream, the gas stream may be transported to a natural gas processing facility. The transporting step may comprise moving a natural gas production stream from a wellhead to the reactor by means of a pipeline. Alternatively, natural gas may be moved to the reactor by rail car or by over-the-road tank. Alternatively still, the reactor may be located at a well head or a local gathering facility and connected to a heater treater or other separator so that methane and ethane are flashed off of liquid components and immediately captured.

In one aspect, the process further comprises removing any $H_2O$, from the natural gas production stream. This may be done before transporting the natural gas production stream to the reactor, or upon delivery of the gas stream to the reactor. In any instance, the dehydrated and sweetened natural gas production stream may be fed to the reactor at a rate of, for example, 0.8 gpm/kW.

It is preferred that the gas stream be pressured to at least 15 psi before introduction into the reactor. It is further preferred that the gas stream be heated to at least 100° F. before or upon introduction of the natural gas production stream into the reactor. In one aspect, both the pressuring and the heating are done through the use of one or more blowers.

The method also includes exposing the natural gas stream to electron beam radiation within the reactor. In one aspect, the gas production stream is moved through an irradiation area within the reactor at a rate of 800 m³/hour. In any instance, the irradiation generates a substantially liquefied hydrocarbon stream according to:

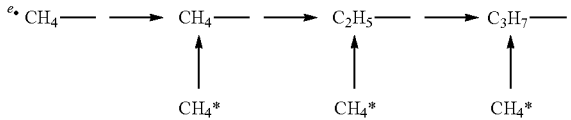

The method further includes transporting the substantially liquefied hydrocarbon stream into a separator. The separator is preferably a dual scrubber tank operated at 110° F. The separator or scrubber may comprise one or more gas-to-liquid centrifugal separators in series. Alternatively, the separator may comprise a shell-and-tube heat exchanger wherein cooling takes place through heat exchange with chilled water. In this instance, the cooling condenses most remaining gaseous components.

Two fluid streams are released from the separator. These represent a first stream of lighter alkanes, being in the $C_1$ to $C_5$ range, and a second stream primarily of heavier hydrocarbons, representing $C_6$ alkanes and higher. The stream of lighter alkanes is a small stream of mostly non-condensed fluids, and is re-circulated back into the reactor as a gas. At the same time, the heavier alkanes, which are more valuable than the lighter alkanes, are in a liquefied state and are moved off-site for sale. Optionally, fractionation of the heavy carbon components is conducted to separate hydrocarbon species. This may be done, for example, by using a distillation column to generate separate condensate streams. In this process, the liquid condensate is heated to progressively higher temperatures that cause the several components to separate through sequential evaporation. The valuable end products of heptane, hexane and residual octane (and above) are generated. All products are produced as a 100 octane condensate.

In one aspect, the method further comprises monitoring the hydrogen ($H_2$) content in the non-condensed fluids (or gases) released from the separator. When the hydrogen content reaches 10% by volume in the non-condensed fluids, the non-condensed fluids are sent to a pressure swing absorption unit (or other separator) for removal of the hydrogen gases. In this instance, re-circulating non-condensed fluids from the substantially liquefied hydrocarbon stream back into the reactor comprises returning the gases after separation of the hydrogen content in the pressure swing absorption unit.

BRIEF DESCRIPTION OF THE DRAWINGS

So that the present inventions can be better understood, certain drawings, charts, graphs and/or flow charts are appended hereto. It is to be noted, however, that the drawings illustrate only selected embodiments of the inventions and are therefore not to be considered limiting of scope, for the inventions may admit to other equally effective embodiments and applications.

DETAILED DESCRIPTION OF CERTAIN EMBODIMENTS

Definitions

As used herein, the term "fluid" refers to gases, liquids, and combinations of gases and liquids.

As used herein, the term "gas" refers to a fluid that is in its vapor phase at 1 atm and 15° C. to 20° C.

As used herein, the term "oil" refers to a hydrocarbon fluid containing primarily a mixture of condensable hydrocarbons.

Preliminary Statement

The inventions are described herein in connection with certain specific embodiments. However, to the extent that the following detailed description is specific to a particular embodiment or a particular use, such is intended to be illustrative only and is not to be construed as limiting the scope of the inventions.

Description of Selected Specific Embodiments

Natural gas is frequently produced from subsurface reservoirs. The primary component of natural gas is the group of light alkanes consisting of methane ($C_1$) and ethane ($C_2$). These are known as saturated acyclic hydrocarbons. Fractions of propane ($C_3$), butane ($C_4$) and pentane ($C_5$) are also found in raw natural gas streams, although these fractions are more commonly liquefied at ambient conditions.

It is desirable to upgrade the otherwise non-condensable components into a higher molecular weight hydrocarbon form for use as a high-octane fuel or for use as a fuel blend. Accordingly, processes are offered herein for converting the gaseous alkanes from a natural gas stream into a 100 octane condensate. Each process involves the continuous exposure of a natural gas source to electron beam radiation to generate heavy hydrocarbon fluids as liquid radiolytic products, and the re-circulation of remaining light alkanes. The processes also involve the removal of hydrogen gas from the light alkanes before re-circulation.

Figure 1:
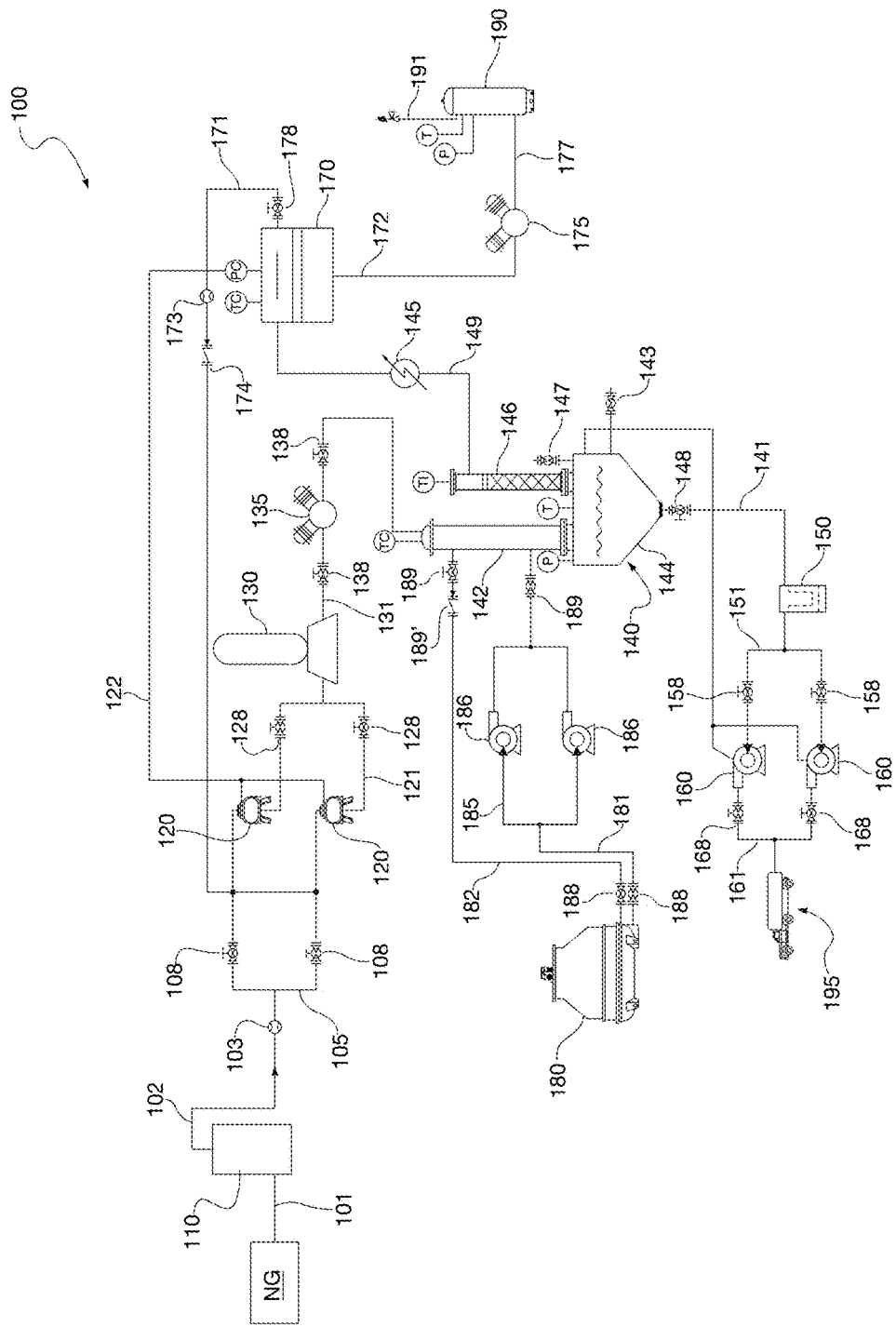
FIG. 1 presents a schematic view of a natural gas separation facility in accordance with the present invention, in one embodiment.

FIG. 1 presents a schematic view of a gas-to-liquids conversion facility 100 in accordance with the present invention, in one embodiment. The facility 100 is used to conduct a radiation-chemical synthesis process wherein gaseous alkanes are converted into higher carbon number radiolysis products for use as a high octane transportation fuel. These radiolysis products are referred to herein at times as "100 octane condensate."

In the system 100, a natural gas source is first shown schematically at "NG." The natural gas NG is preferably associated with oil and gas production operations. In one preferred embodiment, the natural gas NG is a gas production stream located at a production facility or an FPSO. In this instance, the gas NG has been separated from production liquids such as through gravity separation. At many production facilities, a certain amount of natural gas is used on-site as fuel gas, with the remaining gas stream being flared. Thus, in one aspect herein, the natural gas NG represents a gas stream that would otherwise have been flared.

It is understood that the present inventions are not limited to the nature of the source for the natural gas NG. Other sources of light alkanes besides conventional oil and gas production operations may be utilized as the natural gas source NG. These may include gas produced from so-called tight shale formations such as the Barnett Shale or the Eagle Ford shale. These may also include gas obtained from coalbed methane recovery, biomass conversion operations, permafrost melt outgassing and landfill outgassing.

In any of these events, the natural gas source NG is delivered to the facility 100 by means of a transport line 101. The transport line 101 may be a pipeline; alternatively, the line 101 may be an offloading line from a truck, a rail car or a storage tank. In one aspect of operation, 28,000 ft$^3$/hour of natural gas is passed through line 101, or 672,000 ft$^3$/day.

It is observed that in connection with the production or recovery of hydrocarbon gases, natural gas is not always produced in a "clean" form, that is, a gas stream made up almost entirely of methane and ethane ($C_1$-$C_2$); rather, gas production streams will typically include other lighter alkane components such as propane, butane and pentane ($C_3$-$C_5$). In addition, a gas production stream will frequently include non-hydrocarbon elements such as hydrogen, nitrogen, carbon dioxide and hydrogen sulfide, causing the gas to be "sour." Thus, in one embodiment, the facility 100 includes a gas processing system, shown schematically at 110.

The gas processing system 110 may also be used for the removal of water ($H_2O$). This may be done before transporting the natural gas NG to the facility 100, or upon delivery of the light alkanes NG to a locus of the facility 100. Water may be removed through a gravity separator or through cryogenic dehydration. Cryogenic dehydration generally comprises cooling the wet natural gas through Joule-Thomson expansion. Cooling is applied until the components to be removed precipitate by condensation or formation of hydrates.

Water separation may also be accomplished by chemically mixing methanol, glycol or a paraffin solvent into a raw gas stream to cause the water to break out of solution. This is referred to as dehydration by absorption. The water and glycol are then captured through a bottom aqueous stream. Water separation may alternatively be carried out through an adsorptive process using an adsorbent suitable for retaining water. Examples include molecular sieves and silica gels.

The gas processing system 110 may also be used for the removal of carbon dioxide ($CO_2$) and sulfuric components from the natural gas source NG. Sulfuric compounds may include, for example, hydrogen sulfide ($H_2S$) carbonyl sulfide and mercaptans. Processes are known for removing such non-hydrocarbon components from a gas production stream. Such processes are referred to as "sweetening."

Carbon dioxide and sulfur compounds may be removed through any of physical absorption processes, chemical absorption processes, physical-chemical absorption processes, liquid oxidation processes, adsorption processes and membrane processes. Membrane processes used for natural gas separation can be simultaneously performed for removal of carbon dioxide and hydrogen sulfide. Any of these processes are well-known to those of ordinary skill in the art of natural gas processing.

Generally, chemical absorption processes comprise the use of a gas scrubber wherein the sour natural gas components are reversibly bound to a solvent such as an amine by chemical or physical absorption. The scrubber may simply be a series of mixing tanks. Chemical absorption processes generally comprise an alkanolamine scrubbing wherein aqueous solutions of monoethanolamine, di-ethanolamine, di-isopropylamine, di-glycolamine or methyldi-ethanolamine are used as absorbents. After mixing, the solvent undergoes a regeneration step where the sour natural gas components are desorbed unchanged. The solvent is then recycled to a first scrubber.

In physical absorption processes, carbon dioxide and hydrogen sulfide are generally physically dissolved in a solvent. The solvent may be, for example, N-methylpyrrolidone (or Purisol®), methanol (or (Rectisol®), Propylene Carbonate (Fluor Solvent™), a mixture of poly(ethylene glycol dimethyl ether), poly(ethylene glycol methyl isopropyl ether), DEPG (Selexol™ or Coastal AGR®) and propylene carbonate. Physical-chemical absorption processes generally comprise using a combination of solvents in physical absorption and chemical absorption processes.

In instances where the carbon dioxide component is particularly high, the sour gas may first be taken through a Joule-Thompson valve for flash cooling, and then carried into a cryogenic distillation tower or bulk fractionation unit for the removal of $CO_2$. Where the $H_2S$ component is unusually high, the sour gas stream may be flowed across an adsorbent bed. Adsorbent beds operate on the principle that different molecules can have different affinities for adsorption. This provides a mechanism for the adsorbent to discriminate between different gases. The adsorbent is preferably chosen from activated charcoal, iron oxide, zinc oxide and zeolitic molecular sieves.

A typical natural gas stream may also comprise nitrogen. In this instance, the gas processing system may further comprise a purification stage wherein nitrogen ($N_2$) is removed from the natural gas NG. This is particularly applicable where the nitrogen concentration is great than about 2% by volume. Nitrogen is typically removed via membrane separation. In one aspect of the system 100, nitrogen is removed at the back end using membrane separator 170.

It is observed that sweetening processes are required in order to bring a natural gas stream into pipeline specification. Pipeline spec. generally requires the following levels:

| Component | Percentage (mole %) |
|---|---|
| Hydrogen | trace |
| Carbon Monoxide | 0 |
| Carbon Dioxide | 0.7-1.2 |
| Oxygen | 0.02 |
| Methane | 90.0-95.0 |
| Ethane | 2.0-4.5 |
| Propane | 0.2-1.0 |
| i-Butane | 0.1-0.3 |
| n-Butane | 0.01-0.03 |
| i-Pentane | 0.01-0.5 |
| n-Pentane | 0.01-0.03 |
| C6+ | 0 |
| Ethylene | 0 |
| Total | 100 |

Of course, true pipeline spec. gas is not required for the present GTL conversion process as the presence of so-called heavy hydrocarbons (C6+) is actually desirable. $C_6$ through $C_{10}$ alkanes, alkenes and isomeric cycloalkanes are the top components of gasoline, naphtha and jet fuel as well as specialized industrial solvent mixtures.

After gas processing 110 is conducted, the dehydrated and/or sweetened gas is carried out through gas line 102. Line 102 delivers natural gas through an optional flow meter 103, and then to an electron beam reactor 130. At this point, the alkane gas composition may enter the reactor 130 as, for example, 95% $CH_4$ and 5% $C_2H_6$. The natural gas production stream may be fed to the reactor 130 at a rate of, for example, 0.8 gpm/kW. The reactor 130 is an electron beam reactor such as a steel flow-type reactor connected hermetically to an accelerator beam window. This may be referred to as a "pipe and E-beam window" design.

It is preferred that the gas stream be pressured to at least 15 psi before introduction into the reactor 130. It is further preferred that the gas stream be heated to at least 100° F. before or upon introduction of the natural gas stream into the reactor 130. In one aspect, both the pressuring and the heating are done through the use of one or more blowers 120.

In the illustrative facility 100, a pair of blowers 120 is shown. Each blower 120 represents a mechanism for delivering natural gas 110 under slight pressure to the reactor 130. Line 102 splits into separate lines 105 for delivery of natural gas 110 to the blowers 120. Each line 105 includes a gate valve 108 for controlling the flow of natural gas 110 into the respective blowers 120. The blowers 120 may have a 500 scf/minute or greater air handling capacity.

The blowers 120 deliver warmed and compressed gas through lines 121. A gate valve 128 is provided along each line 121 to selectively control gas flow. Warmed and compressed gas then enters the reactor 130 where the gas stream is exposed to electron beam radiation. The gas flow rate in the irradiation zone may vary over the range 500 to 1,000 m³/hour. Preferably, the gas production stream is moved through an irradiation area within the reactor at a rate of about 800 m³/hour.

In one aspect, the flow rate is calculated as:

$$900 \text{ Nm}^3/\text{hour} * 16.7/22.4 = 670 \text{ kg/hour}$$

$$= 0.19 \text{ kg/second}$$

The electron beam may be generated by 1 MeV at 400 kW. The rate of energy consumption may be 0.5 to 2.0 kW/m³ (absorbed dose rate). In one aspect, the e-beam power requirements are:

$$P = 0.5 \text{ kWh/m}^3 * 900 \text{ Nm}^3/\text{h} = 450 \text{ kW/h}$$

The reactor may use, for example, an Avrora-9B UEVK cascade accelerator as a source of electron radiation. The accelerator generates an electron energy of 500 keV, a beam current to 80 mA, and a beam power to 40 kW. The following table demonstrates excitation requirements for low molecular weight hydrocarbon products:

| Compound | Excitation (eV) | Ionization (eV) |
|---|---|---|
| Methane | 9.6 | 13.1 |
| Ethane | 9.4 | 11.6 |
| Propane | 8.9 | 11.2 |
| Butane | 8.7 | 10.8 |
| Pentane | 8.7 | 10.4 |

The irradiation process generates a substantially liquefied hydrocarbon stream according to:

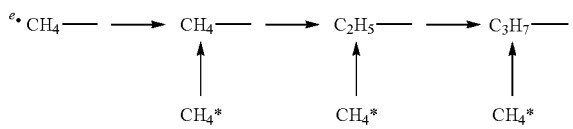

In this process, liquid radiolytic products are accumulated in a mixture of $C_nH_{2n+2}$ and $C_mH_{2m+2}$, as follows:

$$\cdot C_nH_{2n+1} + \cdot C_mH_{2m+1} \Rightarrow C_{n+m}H_{2(n+m)+2}$$

$$\cdot C_nH_{2n+1} C_mH_{2m+2} \Rightarrow C_mH_{2m+1} C_nH_{2n+2}$$

$$\cdot C_nH_{2n+1} C_kH_{2k} \Rightarrow C_{n+k}H_{2(n+k)+1}$$

The light alkalies absorb more energy of ionizing radiation, allowing the growth of alkyl radicals as "radiolysis products."

The absorbed does (D) may be calculated according to one embodiment as:

$$D = P \cdot \varepsilon / M$$
$$= 2{,}000 \text{ kW} * 0.6/0.414 \text{ kg/s}$$
$$= 1{,}450 \text{ kGy}$$

where: $\varepsilon$=efficiency
P=power
M=flow rate

The dose rate may be calculated as:

$$DR = 2{,}000 \text{ kW}/3{,}600 \text{ s} * 0.6/0.414 \text{ kg/s}$$
$$= 0.40 \text{ kGy/s}$$

In another embodiment, the folio wing design parameters may be used:
Flow Rate=2,000 $Nm^3/h$.
Absorbed Dose=30 kGy
Power=20 kW
Residence Time ($T_2$)=0.24 s The required retention time in the e-beam reactor may be calculated according to:

$$T_1 = D1/D2 * T_2$$
$$= 1{,}450/30 * 0.24$$
$$= 12 \text{ minutes}$$

where: D1=total absorbed dose; and
D2=absorbed dose efficiency.

Recirculation is calculated as $$R = T1/T2$$
$$= 12/0.24$$
$$= 50 \text{ turns}$$

Treatment capacity is calculated as $$TC = \text{Flow Rate} * T_2/T_1$$
$$= 2{,}000 * 0.24/50$$
$$= 40 \text{ Nm}^3/h$$
$$= 33{,}600 \text{ ft}^3/\text{day}$$

For a reactor operating at 20 kW, 33,600 $ft^3$/day of natural gas may be processed. For a reactor operating at 400 kW, 672,000 $ft^3$/day of natural gas may be processed.

It is noted that 6,000 $ft^3$/day equates to 1 barrel. 672 mcf/day equates to 112 bbl. At a 94% conversion rate, this equates to 105 bbl/day.

Returning to FIG. 1, a fluid stream of "radiolysis products" is released through line 131. The fluid stream in line 131 represents a mixture of hydrocarbon liquids and gases, but is now substantially liquefied. The mixture is taken through a compressor 135. Gate valves 138 are placed on either side of the compressor 135 to provide selective flow control of fluids through line 131. From there, the radiolysis products are delivered on to a separator 140.

The separator 140 may comprise or one or more gas-to-liquid centrifugal separators in series. Alternatively, the separator 140 may comprise a shell-and-tube (or jacketed tube) heat exchanger wherein cooling takes place through heat exchange with water (+16° C.) and/or boiling propane (−42° C.). In this instance, the cooling condenses most remaining gaseous components so that liquid alkanes are condensed.

In the processing facility 100, line 131 delivers the radiolysis products into the top of a heat exchanger 142. In the illustrative heat exchanger 142, chilled water is used for cooling the radiolysis products as a shell-and-tube heat exchanger. The water is chilled in a cooling tower 180 and then distributed to the exchanger 142 through line 181. Ball valve 188 controls the flow of water from the cooling tower 180 along line 181. The chilled water is optionally divided into two or more lines 185 for delivery to respective pumps 186. A second ball valve 189 resides along re-merged lines 185 to control the flow of chilled water into the heat exchanger 142. After circulating through the heat exchanger 142, the water is returned to the cooling tower 180 via return line 182. Ball valves 188 and 189 and check valve 189' control the return of water to the cooling tower 180 along line 182.

During cooling of the radiolysis products, liquid alkanes gravitationally fall from the heat exchanger 142 and into a lower condensation basin 144. The liquid alkanes represent higher hydrocarbon components such as heptanes, hexanes and octanes. These radiolysis products are released into line 141 for export from the facility 100. At the same time, lighter alkanes and entrained gases such as nitrogen or hydrogen will rise back up into a distillation column 146. These gaseous components optionally exit the column 146 overhead through line 149.

It is observed here that during fluid separation, the separator 140 is carefully monitored and controlled. Temperature control "TC" is shown at the top of the heat exchanger 142 while temperature indicator "TI" is shown at the top of the distillation column 146. Pressure "P" and temperature "T" gauges are provided along the condensation basin 144.

In lieu of using a tube-and-shell type heat exchanger 142 with a chilling tower wherein liquids fall out, the separator may alternatively be a fractionator which fractionates the heavy hydrocarbons, or condensate, in the liquefied stream in the distillation column. In this step, the liquid condensate is heated to specific temperatures that cause the several components to separate through sequential evaporation. It is observed that the boiling points and densities of the respective alkanes increase with an increase in the number of carbon atoms. The boiling points are lower for branched isomers than for slightly branched or linear ones. Components of the condensate are separated into separate products using a vertical fractional distillation system where components are separated into "fractions" based on their boiling properties.

Regardless of the type of separator 140, it can be seen from FIG. 1 that two fluid streams 141, 149 are released from the separator 140. The fluids in line 141 include the heavier hydrocarbons, representing $C_6$ alkanes and higher. The 100 octane (or higher) condensate in line 141 is then sent off-site for further processing or for commercial sale, such as through transport truck 195. In one aspect, the condensate is generated at about 150 bbl/day, comprised of the following general components:

TABLE 3

| Component | Vol. % |
|---|---|
| n-hexane | 40 |
| n-heptane | 40 |
| Octane | 20 |

The lighter alkanes, being in the $C_1$ to $C_5$ range, flow through line 149 and are recirculated back into the reactor 130. A liquid sample port 143 is provided below a fluid level for the condensation basin 144 for testing the condensate. The products of radiolysis may be analyzed using a Q-Mass Perkin-Elmer chromatograph—mass spectrometer wherein helium is a carrier gas. Similarly, a gas sample port 147 is provided at the top of the condensation basin 144 or near a bottom of the distillation column 146 for sampling gases.

Referring to line 149, gaseous components representing a small stream of the lighter, non-condensed alkanes NG are re-circulated back into the reactor 130. The gaseous components are optionally heated at heater 145, and are then delivered to a separator 170 for the removal of hydrogen. In the arrangement of FIG. 1, the depicted separator 170 is a membrane separator.

Generally, membrane separator use the following process steps: (i) absorption of an impurity from the gas phase into a membrane matrix, (ii) diffusion through the membrane, and (iii) desorption out of the membrane and into the gas phase. Membranes generally are polymer membranes preferably chosen from asymmetric cellulose acetate or triacetate, composite layers of silicone/polysulfone, composite layers of polyetherimide, and composite layers of silicone/polycarbonate.

In one embodiment, the membrane separator is a PRISM separator. The following table (Table 1) demonstrates operating conditions for a membrane separator, in one aspect:

TABLE 1

| Feed Pressure (psia) | 18 |
|---|---|
| Feed Temperature (° F.) | 100 |
| Feed Flow Rate (lb-mol/hour) | 8,900 |
| Feed Stream Composition (mol %) | |
| $H_2$ | 63.6 |
| Methane | 8.9 |
| Ethane | 7.1 |

TABLE 1-continued

| Propane | 17.5 |
|---|---|
| n-Butane | 2.7 |
| n-Pentane | 0.2 |

The following table (Table 2) demonstrates hydrogen and hydrocarbon gas output specifications for the membrane separator, in one aspect:

TABLE 2

| $H_2$ Rich Stream | |
|---|---|
| $H_2$ Purity (mol %) | 98.2 |
| $H_2$ Removal (scfm) | 1,800 |
| Flow Rate (scfm) | 1,833 |
| Pressure | 18 |
| Temperature (F.) | 140 |
| Product Stream | |
| $H_2$ Content (mol %) | 29.7 |
| Flow Rate (scfm) | 1,866 |
| Pressure (pisa) | 130 |
| Temperature (F.) | 143 |

Hydrogen is removed from the membrane separator 170 through release line 172. The hydrogen gas is taken through a compressor 175, and then delivered under pressure to a hydrogen storage tank 190. Line 177 indicates a pressurized hydrogen line that feeds into the tank 190. Pressure "P" and temperature "T" gauges are provided for monitoring conditions within the tank 190. When the tank 190 is deemed full, hydrogen may be sent off-site for sale or re-use in another commercial context.

In one aspect, the gases escaping from the lower condensate basin 144 are monitored for hydrogen ($H_2$) content. Hydrogen ($H_2$) content may be monitored by using an $H_2$ sensor proximate a discharge line (147 or 149) from the reactor 140. When the hydrogen content reaches 10% by volume in the non-condensed gases, the gases are then sent to the membrane separator 170. Alternatively, the gases in line 149 may be sent to a pressure swing absorption ("PSA") unit (not shown) for removal of the hydrogen gases. In this instance, re-circulating non-condensed gases in line 149 back into the reactor 130 comprises returning the non-condensed gases after separation of the hydrogen content in the pressure swing absorption unit.

In PSA processes, a gaseous mixture is carried under pressure for a period of time over a first bed of a solid sorbent that is selective, or relatively selective, for one or more components, usually regarded as a contaminant, that is to be removed from the gaseous mixture. The components that are selectively adsorbed are referred to as the heavy component, while the weakly adsorbed components that pass through the bed are referred to as the light components. Thus, the molecular species that do not selectively fill the micropores or open volume of the adsorbent are usually the "light" components.

Adsorbents for PSA systems are usually very porous materials chosen because of their large surface area. Typical adsorbents are activated carbons, silica gels, aluminas and zeolites. In some cases, a polymeric material can be used as the adsorbent material. Though the gas adsorbed on the interior surfaces of microporous materials may consist of a layer of only one, or at most a few molecules thick, surface areas of several hundred square meters per gram enable the adsorption of a significant portion of the adsorbent's weight in gas.

Different molecules can have different affinities for adsorption into the pore structure or open volume of the adsorbent. This provides one mechanism for the adsorbent to discriminate between different gases. In addition to their affinity for different gases, zeolites and some types of activated carbons, called carbon molecular sieves, may utilize their molecular sieve characteristics to exclude or slow the diffusion of some gas molecules into their structure. This provides a mechanism for selective adsorption based on the size of the molecules and usually restricts the ability of the larger molecules to be adsorbed. Either of these mechanisms can be employed to selectively fill the micropore structure of an adsorbent with one or more species from a multi-component gas mixture.

In the present case, hydrogen molecules are considered to be the contaminant. The pressure swing absorption unit, or "PSA," is preferably operated to remove hydrogen at 100 psi, and is maintained at 120° F. (or higher) to ensure that no condensation occurs in the vessels.

Whether using a membrane separator or a PSA unit, excess hydrogen can be captured and re-purposed. For example, $H_2$ may be used in fuel cell vehicles. See http://www.consumerenergycenter.org/transportation/fuelcell/index.html Referring again to the separator 170, conditions within the separator 170 are monitored. Temperature control "TC" and pressure control "PC" systems are associated with the separator 170. In one aspect, a gas line 122 is teed off of the blowers 120 to inject heated gas, under modest pressure, into the separator 170.

Hydrocarbon gases are released from the separator 170 through return line 171. Gate valve 178 provides selective control of gases along return line 171. In addition, a flow meter 173 and a check valve 179 are provided along return line 171. Low carbon gases are delivered back to gas lines 105 where they are ultimately returned to the reactor 130 for radiolytic treatment.

As noted, the heavier alkanes, or condensate, which are more valuable than the lighter alkanes, are in a liquefied state and are released through line 141. In one aspect, the liquid components are moved on to a separate distillation column (not shown) where the heavy hydrocarbons undergo fractionation. In this process, the liquid condensate is heated to progressively higher temperatures that cause the several components to separate through sequential evaporation. Components of the condensate are separated into separate carbon products using a vertical fractional distillation system where components are separated into "fractions" based on their boiling properties. The valuable end products of heptane, hexane and octane (and above) are generated, with each product exiting the column at a different vertical location. All products are produced as a 100 octane condensate Those of ordinary skill in the art will understand that there are other types of fractionation besides distillation/condensation. These include fractionation by molecular filtration, preferably by means of semi-permeable and selective membrane, fractionation by adsorption, preferably by means of molecular sieve, fractionation by absorption, in particular by means of absorbing oil, fractionation by cryogenic expansion, in particular by means of expansion turbine, and fractionation by compression, preferably by means of gas compressor. Any of these may be employed in the present inventions.

The condensate in line 141 may optionally be filtered. FIG. 1 demonstrates a double filter 150. The double filter 150 is capable of processing material at 1,224.73 lbs/hour. Filtered condensate is then released through line 151, and then lightly compressed using one or more blowers 161. Gate valves 158 and 168 are placed on opposing sides of the blowers 160 to control fluid flow to the transport truck 195. Loading line 161 is provided for delivery of valuable end products of heptanes, hexanes, octanes (and above) to the truck 195. All products are produced as a 100 octane condensate.

Figure 2A:
FIG. 2A presents a table showing components of a condensate product stream, in one embodiment.
Figure 2B:
FIG. 2B presents a table showing components of a condensate product stream, in a second embodiment.

FIG. 2A presents a table showing the composition of a final condensate product stream, as one example. FIG. 2B presents a table showing components of a condensate product stream, in a second embodiment.

As can be seen, a process for converting natural gas into hydrocarbon liquids through electron radiation, liquid condensation, and distillation is provided. While it will be apparent that the inventions herein described are well calculated to achieve the benefits and advantages set forth above, it will be appreciated that the inventions are susceptible to modification, variation and change without departing from the spirit thereof.

What is claimed is:

1. A process for converting a gas stream comprising primarily a mixture of light alkanes into a high-octane liquid stream, comprising: transporting the gas stream to a reactor at a gas processing facility; introducing the gas stream into a reactor whereupon components of the gas stream are exposed to electron beam radiation within the reactor to increase the molecular weight of hydrocarbons in the gas stream, thereby producing an upgraded radiolysis fluid stream; transporting the radiolysis fluid stream into a separator, thereby producing a first gaseous stream comprising primarily light alkanes, and a second liquid stream comprising primarily heavy alkanes; re-circulating the first stream back into an inlet of the reactor for additional irradiation and upgrading; and transporting the liquid stream off-site for further processing or for commercial sale, wherein the liquid stream comprises a transportation fuel having an octane rating of at least 100; transporting the second liquid stream as condensate to a distillation column; and fractionating the condensate into separate products comprising at least heptane (and heptane isomers), hexane (and hexane isomers) and octane; and transporting the natural gas stream comprises moving at least a portion of the natural gas stream through a pipeline; and the process further comprises sweetening the gas stream before introduction into the reactor, wherein the gas stream originates from a natural gas stream incident to oil and gas production operations; and transporting the natural gas stream to a reactor comprises moving the natural gas stream from a wellhead or from a field gathering facility to the reactor, the separator comprises a shell-and-tube heat exchanger for chilling the radiolysis fluid stream, and a distillation column for capturing non-condensable fluids, and the electron beam is generated by 1 MeV at 400 kW.

2. The process of claim 1, wherein the gas stream is a natural gas stream, an artificial gaseous alkane mixture, or gaseous industrial waste.

3. The process of claim 1, wherein: the gas stream originates from a natural gas stream incident to oil and gas production operations; and transporting the natural gas stream to a reactor comprises moving the natural gas stream from a wellhead or from a field gathering facility to the reactor.

4. The process of claim 3, further comprising: (i) removing any $H_2O$ from the natural gas stream before introducing the natural gas stream into the reactor, (ii) removing any $CO_2$ from the natural gas stream before introducing the natural gas stream into the reactor, (ii) removing any H.sub.2S from the natural gas stream before introducing the natural gas stream into the reactor, or (iii) combinations thereof.

5. The process of claim 4, further comprising: pressuring the natural gas stream to at least 15 psi, and heating the natural gas stream to at least 100.degree. F. before introducing the natural gas stream into the reactor.

6. The process of claim 5, wherein pressuring and heating the natural gas production stream is done through the use of at least one blower.

7. The process of claim 5, wherein the separate comprises one or more gas-liquid centrifugal separators in series.

8. The process of claim 5, further comprising: monitoring the hydrogen (H.sub.2) content in the first gaseous stream released from the separator; and when the hydrogen content reaches 10% by volume in the first gaseous stream, sending non-condensed gases of the first gaseous stream to a hydrogen separator for removal of hydrogen gases before the first gaseous stream is re-circulated back into the reactor for additional irradiation and upgrading.

9. The process of claim 8, wherein: monitoring the hydrogen (H. sub.2) content is done by using an H. sub.2 sensor proximate a discharge line from the reactor; and the hydrogen separator is removed from the gas mixture by either a membrane separator or a pressure swing absorption unit.

10. The process of claim 9, wherein: excess hydrogen is removed from the non-condensed gases by a pressure swing absorption unit; and the pressure swing absorption unit is operated at 100 psi and contains (i) activated carbon, (ii) zeolite, or (iii) a combination thereof.

11. The process of claim 10, wherein the pressure swing absorption unit is maintained at 120.degree. F. or higher.

12. The process of claim 1, further comprising: before re-circulating, removing hydrogen gas from the first gaseous stream using a membrane separator.

13. The process of claim 1, wherein the reactor is a steel flow-type reactor connected hermetically to an accelerator beam window.

14. The process of claim 1, wherein: the gas production stream is moved through an irradiation area within the reactor at a rate of 800 m.sup.3/hour; and a rate of energy consumption for an absorbed dose rate is 2.0 kW/m.sup.3.

15. The process of claim 1, further comprising: blending at least a portion of the liquid stream as a condensate product into a lower-octane fuel to generate a higher octane transportation fuel.

* * * * *